(12) United States Patent
Bonner et al.

(10) Patent No.: US 8,504,156 B2
(45) Date of Patent: Aug. 6, 2013

(54) HOLDING MEMBERS FOR IMPLANTABLE CARDIAC STIMULATION DEVICES

(75) Inventors: Matthew D. Bonner, Plymouth, MN (US); Thomas A. Anderson, New Hope, MN (US); William A. Berthiaume, Santa Rosa, CA (US); Noelle C. Hurtig, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/219,279

(22) Filed: Aug. 26, 2011

(65) Prior Publication Data

US 2013/0053921 A1 Feb. 28, 2013

(51) Int. Cl.
*A61N 1/00* (2006.01)
(52) U.S. Cl.
USPC .................................................... 607/36
(58) Field of Classification Search
USPC ................... 607/115–132, 2–28, 36, 37
See application file for complete search history.

(56) References Cited

U.S. PATENT DOCUMENTS

| 3,835,864 | A  | 9/1974  | Rasor et al. |
| 7,444,180 | B2 | 10/2008 | Kuzma et al. |
| 7,857,819 | B2 | 12/2010 | Jaax et al. |
| 2005/0267555 | A1* | 12/2005 | Marnfeldt et al. ............ 607/116 |
| 2010/0198288 | A1  | 8/2010  | Ostroff |
| 2012/0172892 | A1* | 7/2012  | Grubac et al. ................ 606/129 |

FOREIGN PATENT DOCUMENTS

| WO | 03/032807 A2 | 4/2003 |
| WO | 2012/092074 A1 | 7/2012 |

OTHER PUBLICATIONS (PCT/US2012/049264) PCT Notification of Transmittal of the International Search Report and the Written Opinion of the International Searching Authority.

* cited by examiner

*Primary Examiner* — Scott Getzow
(74) *Attorney, Agent, or Firm* — Reed A. Duthler

(57) ABSTRACT

A holding member for an implantable cardiac device facilitates tether attachment and removal, at time of implant, and snaring, or otherwise capturing, for subsequent explant. Preferably located in proximity to a proximal end wall of a shell of the device, the holding member includes a strut portion, being spaced proximally apart from the proximal end wall, a waist portion, defining a recess, and an engagement section, extending between the strut portion and the waist portion and overhanging the recess. The waist portion may either extend between the strut portion and the proximal end wall, or be formed in the shell, distal to the proximal end wall. Alternately, the holding member includes a loop element and an engagement element coupled thereto, between first and second segments thereof. The segments are initially formed to give the loop element an opening, and have a flexibility to be compressed together.

8 Claims, 7 Drawing Sheets

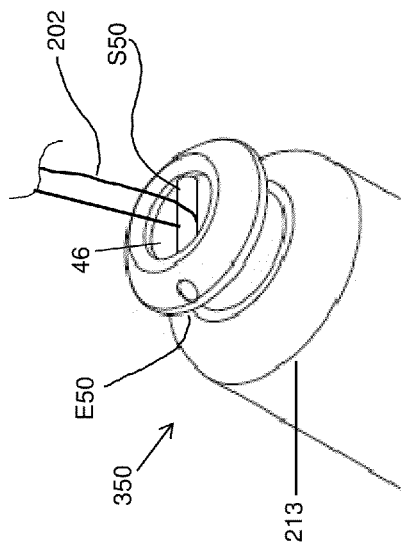
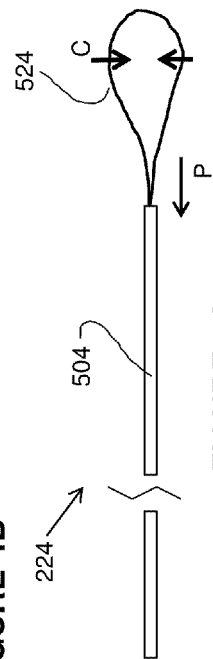
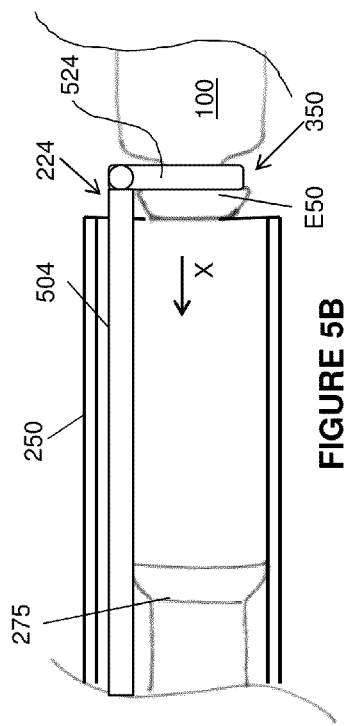
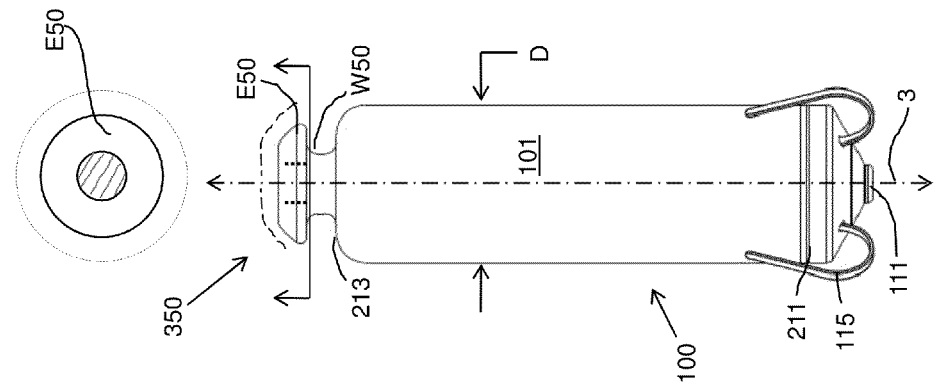

HOLDING MEMBERS FOR IMPLANTABLE CARDIAC STIMULATION DEVICES

TECHNICAL FIELD

The present invention pertains to implantable cardiac devices and more particularly to features thereof that facilitate implant and explant.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of cardiac pacing devices that are wholly contained within a relatively compact package for implant in close proximity to the pacing site, for example, within the right ventricle (RV) of the heart. With reference to FIG. 1, such a device 100 is illustrated, wherein pace/sense electrodes 111, 112 are formed on an exterior surface of a shell 101 that hermetically contains pulse generator electronics and a power source. FIG. 1 further illustrates a fixation member 115 mounted to an end of shell 101, in proximity to electrode 111, in order to fix, or secure electrode 111 against the endocardial surface of RV, and electrode 112 offset distally from electrode 111. Shell 101 is preferably formed from a biocompatible and biostable metal such as titanium overlaid with an insulative layer, for example, medical grade polyurethane or silicone, except where electrode 112 is formed as an exposed portion of capsule 101. A hermetic feedthrough assembly (not shown), such as any known to those skilled in the art, couples electrode 111 to a pulse generator contained within shell 101.

Any one of a number of fixed shape or steerable delivery catheters, which are known in the art, can be employed to deliver device 100 into the heart for implantation, for example, by a transvenous femoral approach, via percutaneous entry. With reference to FIG. 2A, a delivery catheter 20 is shown extending up through the inferior vena cava IVC and into the right ventricle RV via passage through the right atrium RA and tricuspid valve. A distal portion 250 of catheter 20, in which device 100 is initially fitted for delivery into the RV, is shown pulled back from the implanted device 100, for example, to conduct an implant evaluation (i.e. sensing and pacing threshold testing). FIG. 2A illustrates a temporary tether 202 joining device 100 to catheter 20 so that, if results of the implant evaluation indicate that the implant site for device 100 should be adjusted, tether 202 may be used to pull device 100 back into distal portion 250 of catheter 20 for repositioning. Once device 100 is implanted at an appropriate site, tether 202 is separated therefrom, according to any suitable method known in the art. With reference to FIG. 2B, if subsequent explant of device 100 is necessary, a retrieval snare 224, such as any suitable type known to those skilled in the art, may be employed.

SUMMARY

Embodiments of the present invention are directed toward various configurations of holding members for implantable cardiac devices, which configurations facilitate both initial temporary tether attachment and removal, at the time of implant, and subsequent snaring, or otherwise capturing, for explant of the device after the tether has been removed. A holding member, which is preferably located in proximity to a proximal end wall of a shell of a device, for example, at an opposite end of the device from a fixation member of the device, includes a tether feature in conjunction with a capture feature, according to some preferred embodiments.

According to some embodiments, the tether feature of a holding member is formed by a strut portion, which is spaced proximally apart from the proximal end wall; and the capture feature is formed by a waist portion, which defines a recess, and an engagement section, which extends between the strut portion and the waist portion and which overhangs the recess. The waist portion may either extend between the strut portion and the proximal end wall, or be formed in the shell, distal to the proximal end wall.

According to some alternate embodiments, a holding member includes a loop element and an engagement element coupled thereto, between first and second segments of the loop element. The first and second segments have terminal ends coupled to the device, preferably in proximity to the proximal end wall; and the segments, which are initially formed to give the loop element an opening for tether attachment and removal, have a flexibility to be compressed together between the engagement element and the proximal end wall, for example, by snaring at the time of explant. A maximum dimension of a radial profile of the compressed together segments is preferably less than a maximum dimension of a radial profile of the engagement element.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements.

FIG. 4A is a plan view alongside a corresponding cross-section view, which are approximately to scale, of another embodiment;

FIG. 4B is a partial perspective view of the embodiment of FIG. 4A; and

FIG. 5A is a plan view of an exemplary retrieval snare.

FIG. 5B is a plan view of the snare engaged with the embodiment of FIGS. 4A-B.

DETAILED DESCRIPTION

Figure 1:
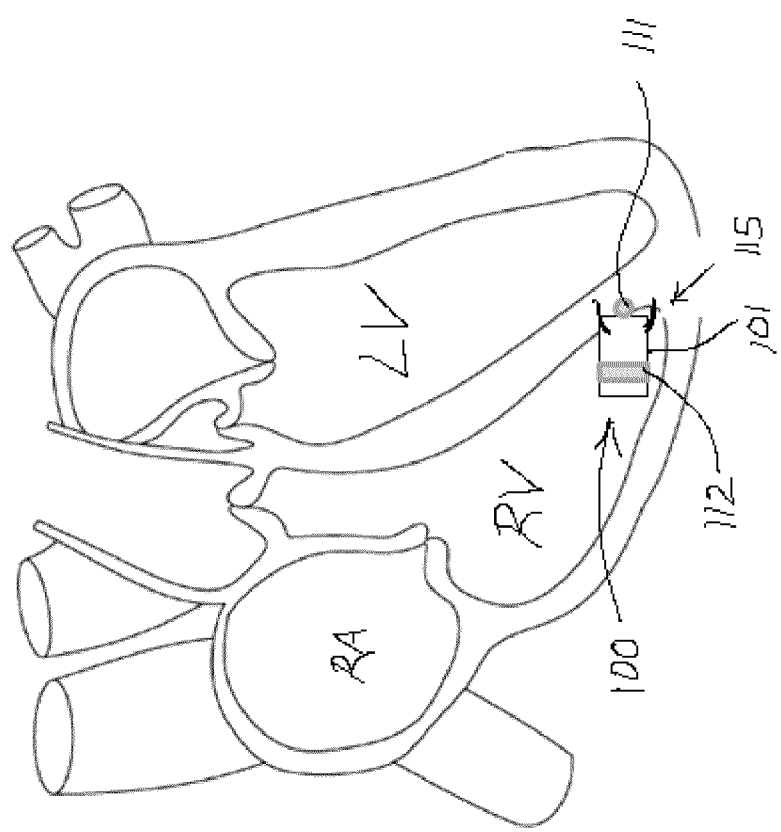
FIG. 1 is a schematic providing some context for embodiments of the present invention.

The following detailed description is exemplary in nature and is not intended to limit the scope, applicability, or configuration of the invention in any way. Rather, the following description provides practical examples, and those skilled in the art will recognize that some of the examples may have suitable alternatives.

FIGS. 3A-D and 4A are plan views alongside corresponding cross-section views of various embodiments of implantable cardiac stimulation device 100, wherein each includes a holding member 310, 320, 330, 340 and 350 located in proximity to a proximal end wall 213 of shell 101, which hermetically contains pulse generator electronics and a power source (not shown) of each device 100, as described above. With further reference to FIGS. 3A-D and 4A, fixation member 115 is shown located at an opposite end of each device, in proximity to a distal end wall 211 of shell 101, in order to secure electrode 111 against cardiac tissue at the implant site. It should be noted that the reference numeral 100 is used for each device in all of the Figures for the sake of simplicity, and that reference numerals for the aforementioned distal end wall, fixation member, and electrode, as well as reference numeral 3, which designates a longitudinal axis of each device, are only shown in FIGS. 3A and 4A, likewise for the sake of simplicity in illustration, and since these features may be common for device 100 among the various embodiments of holding members shown in FIGS. 3A-D and 4A. Each of holding members 310-350 includes a strut portion S, for temporary tether attachment, and an engagement section E in combination with a waist portion W, which defines a recess, for capture by, and attachment thereto of a retrieval snare, like snare 224 shown in FIGS. 2B and 5A-B, or another type of explant tool, for example, like that shown in FIG. 3E. The location of holding members 310-350, in proximity to proximal end wall 213 of shell 101, is preferred in order to align a pulling force, applied by either a tether or an explant tool, as closely as possible with longitudinal axis 3 of device 100. Each of holding members 310-350 may be formed from a relatively hard biocompatible and biostable metal, for example, an appropriate grade of titanium and then laser welded to shell 101; alternately holding members may be directly formed in the same material blank from which shell 101 is also formed. According to alternate embodiments, any of holding members 310-350 may be formed from an appropriate grade of relatively hard biocompatible and biostable plastic, for example PEEK or polyurethane, which is either insert molded onto locking features of shell 101 or molded and then attached to shell 101 via interlocking features, according to methods known to those skilled in the art.

Figure 2A:
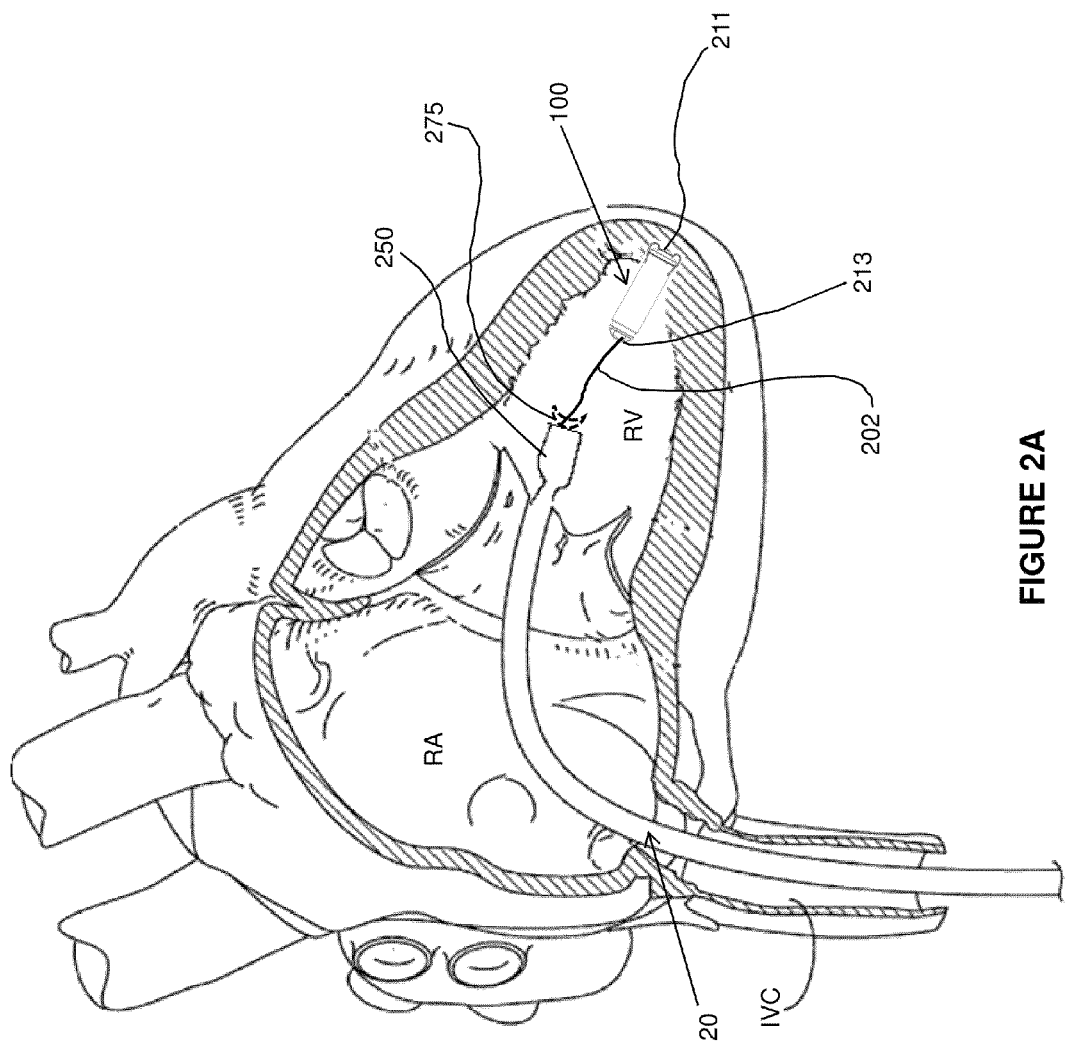
FIGS. 2A-B are schematics illustrating general methods used to implant and explant, respectively, an implanted device.
Figure 3C:
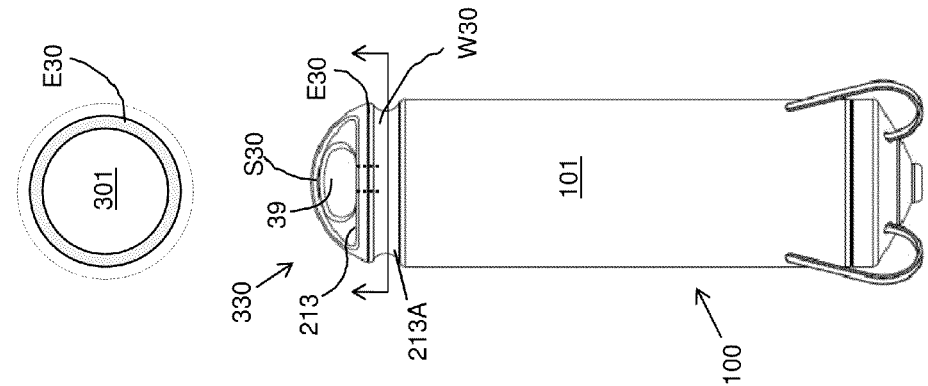
FIGS. 3A-C are plan views alongside corresponding cross-section views, which are approximately to scale, of various embodiments of the present invention.
Figure 3B:
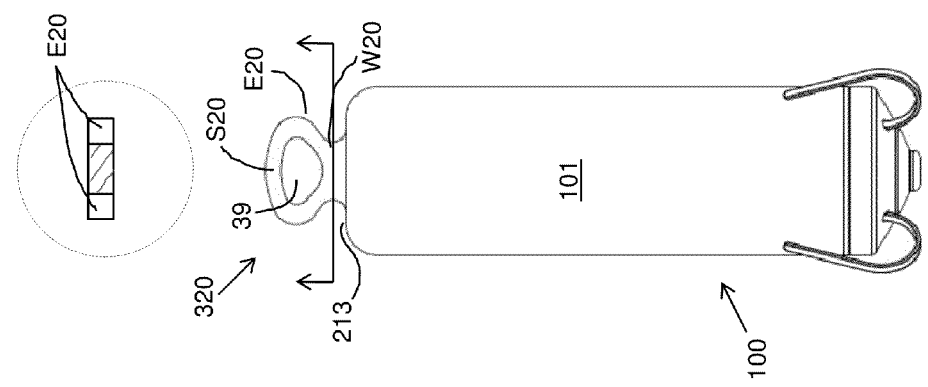
Figure 3A:
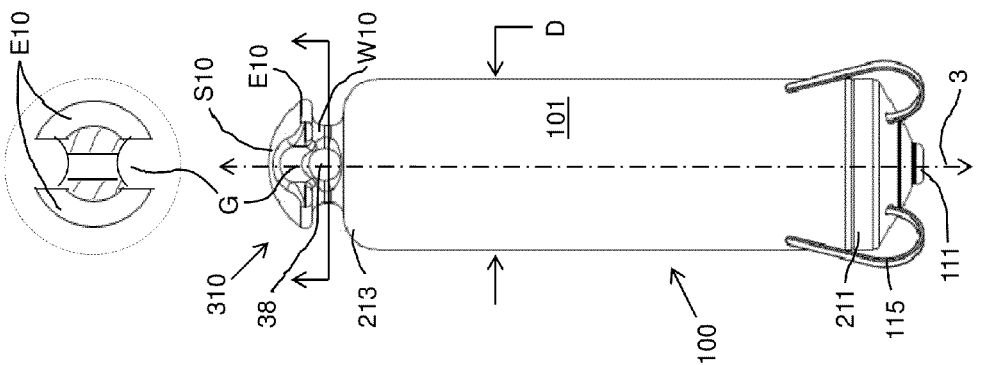

FIG. 3A illustrates strut portion S10 of holding member 310 arching over an eyelet 38 formed through waist portion W10. According to the illustrated embodiment, eyelet 38 allows for attachment and subsequent removal of a temporary tether to strut portion S10; and waist portion W10 provides an area about which a snare member can be tightened and secured, while engagement section E10, which overhangs the recess defined by waist portion W10, allows the tightened snare to apply a pull force generally along axis 3 of device 100. Engagement section E10 extends almost 360 degrees about a perimeter of waist portion W10, being interrupted by an open groove G extending approximately parallel with axis 3, one on each side of holding member 310 (as best seen in the cross-section view of FIG. 3A). Groove G is preferably dimensioned to accommodate a radial cross-section of a segment of either a tether or a retrieval snare. Groove G can provide even closer alignment, along longitudinal axis 3, of the force, applied by tether or snare, and may further keep a radial profile of holding member 310 from being unduly enlarged by the attachment of either thereto. According to some preferred embodiments, a maximum dimension of the radial profile of holding members 310-350 (in this case, the diameter of engagement section E10) is less than a maximum diameter D of shell 101, so that an inner diameter (illustrated by the dotted line in the cross-section view of each of FIGS. 3A-D and 4A) of a distal portion of a delivery catheter, for example, distal portion 250 of catheter 20 (FIGS. 2A and 5B), need not be any larger than necessary to accommodate device 100 in conjunction with the attached tether or snare member. Groove G can allow for an increased outer diameter of engagement section E10 to match maximum diameter D, according to some alternate embodiments. Furthermore, such grooves may be included in other embodiments, for example, as illustrated by dashed lines in FIGS. 3C and 4A. According to some exemplary embodiments, maximum diameter D is between approximately 5 mm and approximately 7 mm.

Figure 2B:
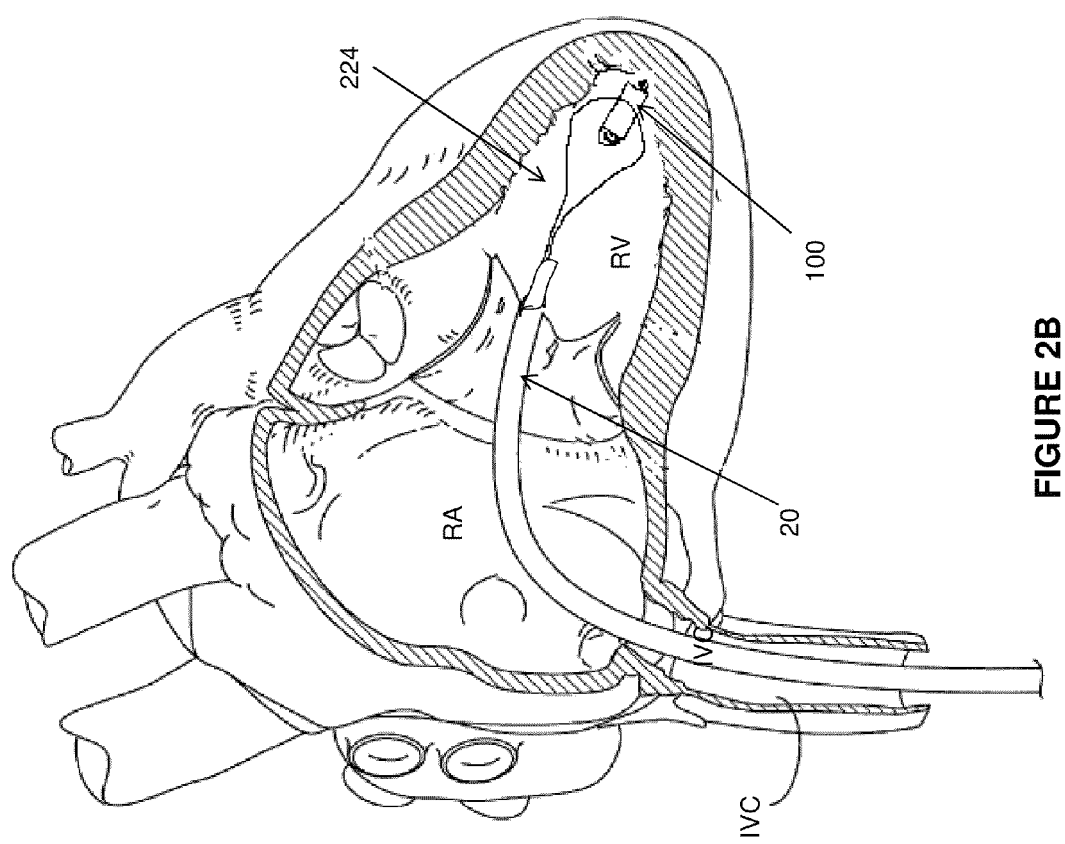
Figure 3E:
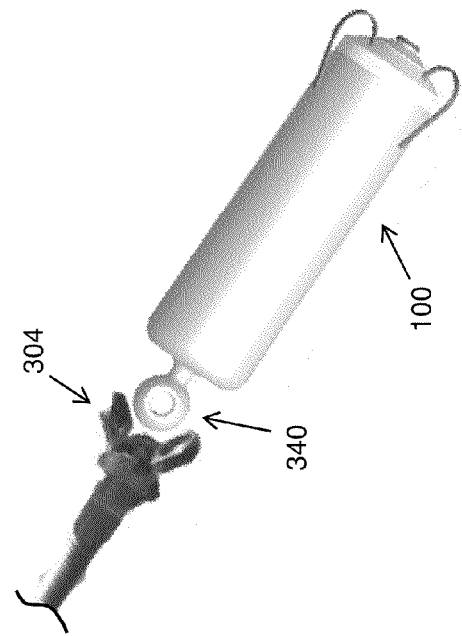
FIG. 3E is a schematic illustrating an alternative extraction tool in conjunction with the embodiment of FIG. 3D.
Figure 3D:
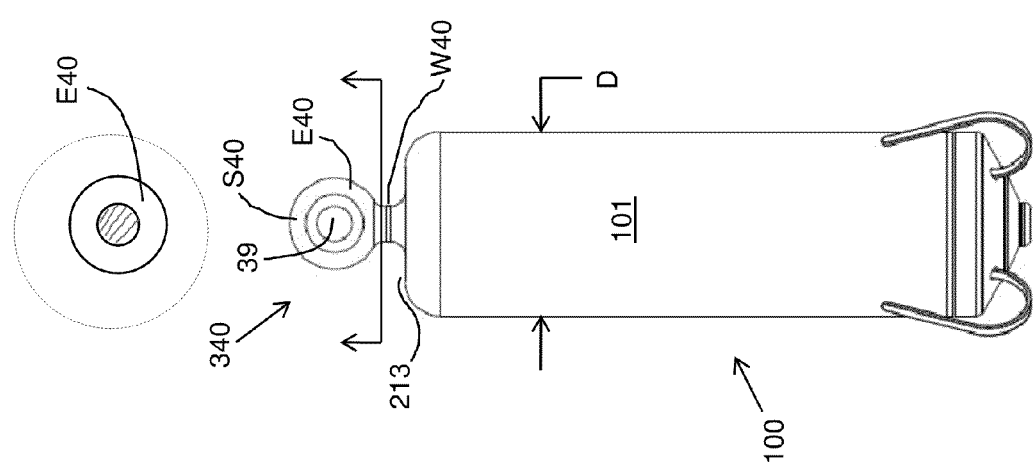
FIG. 3D is a plan view alongside a corresponding cross-section view, which are approximately to scale, of another embodiment.

FIGS. 3B-D illustrate each of holding members 320, 330, 340 including an eyelet 39 formed by the corresponding strut portion S20, S30, S40 in conjunction with the corresponding engagement section E20, E30, E40. The configuration of holding member 320 (FIG. 3B) allows for a significant enlargement of eyelet 39 without direct impact on waist portion W20, which may be minimized in radial cross-section with respect to both engagement section E20 and maximum diameter D, for example, on the order of 1/10 of diameter D, to enlarge the defined recess. An enlarged eyelet can prevent tether binding/snagging during removal, while a minimized waist portion may increase the ease of capture by a retrieval snare, such as snare 224 shown in FIGS. 2B and 5A-B. Holding member 340 (FIG. 3D) also includes a relatively narrow waist portion W40; and the configuration of holding member 330 (FIG. 3C) also includes an enlarged eyelet 39, but, according to the illustrated embodiment, not such a minimized waist portion. The enlarged eyelet 39 of holding members 320 and 330 may increase the ease with which a tether is detached from respective strut portion S20, S30 following implant of device 100, and may further facilitate an explant tool, other than a snare, to grasp onto strut portions S20, S30, for example, with jaws similar to those illustrated in FIG. 3E. With further reference to FIGS. 3D-E, engagement section E40 has a generally spherical contour, as does an exposed surface of strut portion S40. According to the illustrated embodiment, strut portion S40 together with engagement section E40 form a generally spherical member that is suited for grasping within a pair of jaws 304 of a tool that may be employed, rather than the aforementioned retrieval snare, to explant an implanted device 100.

With reference back to FIG. 3C, waist portion W30 of holding member 330 is shown formed in shell 101, just distal to proximal end wall 213, so that holding member 330 is relatively longitudinally compact, to minimize an overall length of device 100. However, according to the illustrated embodiment, waist portion W30 may be constrained by internal space requirements of shell 101, such that the recess defined thereby is not as large as that in other holding member embodiments. The internal space, which is designated by reference numeral 301 in the cross-section view of FIG. 3C, may be dimensioned to accommodate the enclosure of a battery power source for device 100. Alternately, a proximal end wall of shell, which is designated with reference numeral 213A, may be located distal to waist portion W30, similar to other embodiments, in order to reduce a radial cross-section of waist portion W30 and enlarge the defined recess in exchange for some added length to device 100. For reference, a preferred maximum length of device 100 is between approximately 20 mm and approximately 25 mm.

Turning now to FIGS. 4A-B, holding member 350 includes a strut portion S50 formed as a bar that is supported by engagement section E50 within a cavity 46 thereof; and FIG. 4B illustrates tether 202 attached to strut portion S50. The illustrated location of strut member S50 makes holding member 350 relatively compact, while cavity 46 provides sufficient space around strut portion S50 for tether to pull through for removal from strut portion S50 without binding/snagging. Furthermore, the location of strut member S50 does not impact a contour of the proximal-most end of engagement section E50, which contour, according to some preferred embodiments, is tailored to fit snugly within a push member 275, which is shown with dashed lines in FIGS. 2A and in 5B, and illustrated in FIG. 4A by dashed lines that represent an inner contour thereof. Push member 275 is preferably attached to a distal end of an elongate tube, which is slidably engaged within catheter 20 and employed to push device 100 out from distal portion 250 and into engagement, via fixation member 115, with tissue at the implant site.

FIG. 4A further illustrates a relatively large engagement section E50, with respect to a radial cross-section of waist portion W50, such that the recess defined by waist portion W50, in combination with engagement section E50 provide an ample area for retrieval snare 224 to capture device 100. With reference to FIG. 5A, retrieval snare 224 is shown including an elongate tubular member 504 and a snare member 524 that extends within a length of tubular member 504 and out a distal end thereof. FIG. 5A shows snare member 524 in an open position for the initial capture of device 100 therewithin. Once positioned around any of holding members 310-350, snare member 524 is pulled within tubular member 504, per arrow P, such that opposite sides of snare member 524 come together, per arrows C, and tighten around the waist portion W of any of the holding members, for example as shown in FIG. 5B for holding member 350.

FIG. 5B illustrates retrieval snare 224 engaged with holding member 350 to pull device in direction X, such that tubular member 504, into which snare member 524 has been pulled for the tightening around waist portion W50, extends alongside engagement section E50. FIG. 5B further illustrates retrieval snare 224 bringing device 100 into distal portion 250 of catheter 20, which has, preferably, delivered snare into proximity with device 100, for example, as shown in FIG. 2B, and, preferably, remains in place to receive and then enclose the explanted device 100 along an exit path through the upstream venous system. With reference back to the cross-section view of FIG. 4A, the maximum dimension of the radial profile of holding member 350 (in this case, a maximum diameter of engagement section E50), alongside which tubular member 504 of retrieval snare 224 extends, is preferably sized so that holding member 350 and tubular member 504 will fit, side-by-side, within distal portion 250 of catheter 20, whose inner diameter (illustrated by dotted lines in FIG. 4A and shown in longitudinal section in FIG. 5B) is sized no larger than necessary to accommodate diameter D of device 100. According to some alternate embodiments, engagement section 50 has an open groove, like groove G of holding member 310 (FIG. 3A), as indicated by a pair of parallel dashed lines in FIG. 4A, to accommodate retrieval snare 224, for example, if the maximum dimension of the radial profile of engagement section E50 is enlarged to approach the inner diameter of catheter distal portion 250.

Figure 6B:
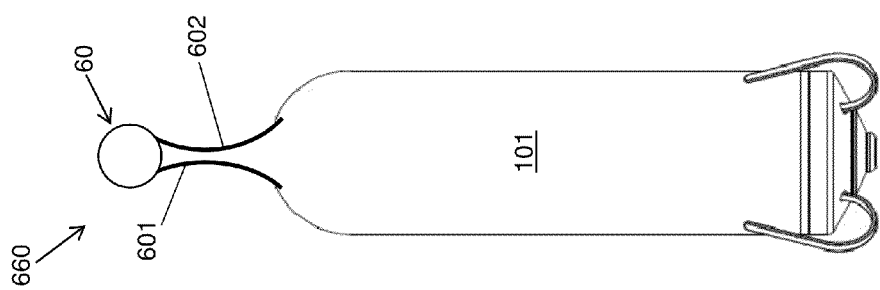
FIGS. 6A-B are plan views of yet another embodiment of the present invention, in first and second states, respectively.
Figure 6A:
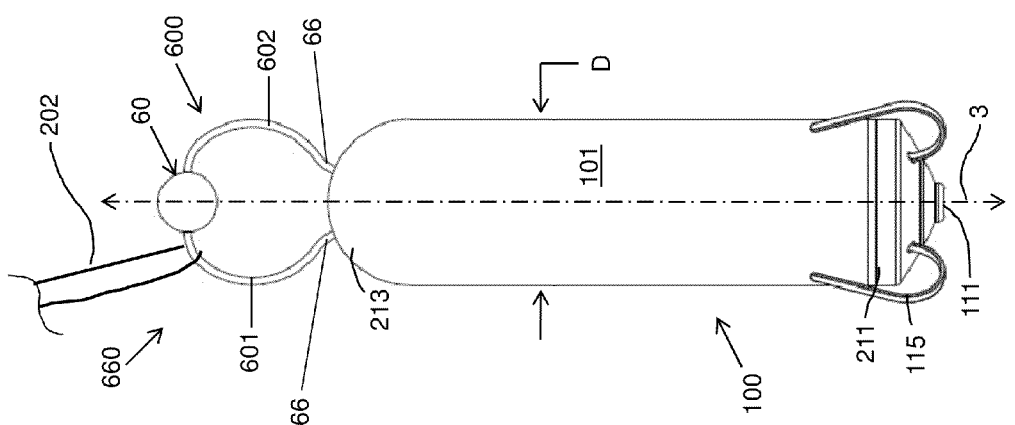

FIGS. 6A-B are plan views of yet another embodiment of present invention. FIGS. 6A-B illustrate device 100 including a holding member 660 located in proximity to proximal end wall 213 of shell 101, wherein holding member 660 includes a loop element 600 and an engagement element 60 coupled thereto. Engagement element 60 is shown coupled to loop element 600, between first and second segments 601, 602 thereof; and each segment 601, 602 is shown including a terminal end 66 coupled to device 100. Segments 601, 602 extend proximally from corresponding terminal ends 66 on opposite sides of device 100 and are initially formed to give loop element 600 an opening located between engagement element 60 and proximal end wall 213, as illustrated in FIG. 6A. Terminal ends 66 of segments 601, 602 may be integral with one another, for example, within proximal end wall 213 of device 100 and extending out through openings in proximal end wall 213. FIG. 6A further illustrates tether 202 attached to loop element 600, and the opening thereof is preferably sufficiently large to accommodate tether removal without snagging/binding. According to the illustrated embodiment, segments 601, 602 bend away from one another, in the proximal direction, in proximity to terminal ends 66 thereof, which may pre-position segments 601, 602 closer together, for subsequent compression into the second state, and/or further facilitate capture of segments 601, 602 within snare member 524, by creating a recess. However, alternate embodiments are not so limited. Furthermore, although engagement element 60 is shown having a generally spherical form, alternate embodiments are not so limited.

According to the illustrated embodiment, first and second segments 601, 602 have a flexibility to compress together from the first state of FIG. 6A, to a second state shown in FIG. 6B. The force compressing segments 601, 602 together may be from the tightening of snare member 524 (FIG. 5A) about loop member 600, and, once compressed together, a maximum dimension of the radial profile of side-by-side segments 601, 602 is smaller than that of the radial profile of engagement element 60, to provide a surface against which the tightened snare member engages to apply a pull force to explant device 100 without itself pulling off holding member 660. Furthermore, the maximum dimension of the radial profile of engagement element 60 is preferably smaller than maximum diameter D of device 100, so that an inner diameter of distal portion 250 of delivery catheter 20 is no larger than necessary. Holding member 660 may be formed of any suitable biocompatible and biostable materials known in the art, examples of which include, without limitation, 316 stainless steel, MP35N and Nitinol. With further reference to FIGS. 6A-B, holding member 660 may be at least partially compressed, for example, between the first state and the second state, within delivery catheter 20, prior to implant, so that an inner diameter of distal portion 250 of catheter 20 need not be any larger than necessary; thus, segments 601, 602, in addition to being flexible, are preferably resilient (i.e. have some spring-like properties), according to some embodiments, in order to expand from a compressed state to an open state, once device 100 is pushed out from distal portion 250 of catheter 20. According to some exemplary embodiments, such segments 601, 602 may be formed from a multi-stranded cable, either MP35N or nitinol, having a PTFE or polyurethane coating; or may be a coil of either MP35N or nitinol, having a polyester fiber core and a PTFE or polyurethane coating.

In the foregoing detailed description, the invention has been described with reference to specific embodiments. However, it may be appreciated that various modifications and changes can be made without departing from the scope of the invention as set forth in the appended claims.

We claim:

1. An implantable cardiac stimulation device including a pulse generator, a power source, a fixation member, a holding member, and a shell; the shell containing the pulse generator and the power source and extending along a longitudinal axis of the device from a proximal end wall to a distal end wall thereof; the fixation member being located in proximity to the distal end wall; and the holding member comprising:

a strut portion spaced apart proximally from the proximal end wall, the strut portion having a span that generally extends in a direction approximately perpendicular to the longitudinal axis of the device;

a waist portion defining a recess that extends between the strut portion and the proximal end wall; and an engagement section extending between the strut portion and the waist portion and overhanging the recess; and wherein the engagement section of the holding member extends approximately 360 degrees about a perimeter of the waist portion of the holding member in a plane that lies approximately orthogonal to the longitudinal axis of the device; and wherein the holding member further comprises an open groove extending along the engagement section in a direction approximately parallel with the longitudinal axis of the device.

2. An implantable cardiac stimulation device including a pulse generator, a power source, a fixation member, a holding member, and a shell; the shell containing the pulse generator and the power source and extending along a longitudinal axis of the device from a proximal end wall to a distal end wall thereof; the fixation member being located in proximity to the distal end wall; and the holding member comprising:

a strut portion spaced apart proximally from the proximal end wall, the strut portion having a span that generally extends in a direction approximately perpendicular to the longitudinal axis of the device;

a waist portion defining a recess that extends between the strut portion and the proximal end wall; and an engagement section extending between the strut portion and the waist portion and overhanging the recess; and wherein the strut portion of the holding member comprises a bar supported by the engagement section; and wherein the engagement section of the holding member includes a cavity within which the bar is supported.

3. An implantable cardiac stimulation device including a pulse generator, a power source, a fixation member, a holding member, and a shell; the shell containing the pulse generator and the power source and extending along a longitudinal axis of the device from a proximal end wall to a distal end wall thereof; the fixation member being located in proximity to the distal end wall; and the holding member comprising:

a strut portion spaced apart proximally from the proximal end wall, the strut portion having a span that generally extends in a direction approximately perpendicular to the longitudinal axis of the device;

a waist portion defining a recess that extends between the strut portion and the proximal end wall; and an engagement section extending between the strut portion and the waist portion and overhanging the recess; and wherein the strut portion of the holding member comprises a bar supported by the engagement section; and wherein the engagement section of the holding member includes a cavity within which the bar is supported.

4. An implantable cardiac stimulation device including a pulse generator, a power source, a fixation member, a holding member, and a shell; the shell containing the pulse generator and the power source and extending along a longitudinal axis of the device from a proximal end wall to a distal end wall thereof; the fixation member being located in proximity to the distal end wall; and the holding member comprising:

a strut portion spaced apart proximally from the proximal end wall, the strut portion having a span that generally extends in a direction approximately perpendicular to the longitudinal axis of the device;

a waist portion defining a recess that extends between the strut portion and the proximal end wall; and an engagement section extending between the strut portion and the waist portion and overhanging the recess; and wherein the strut portion of the holding member arches over an eyelet formed through the waist portion of the holding member, the eyelet extending through the waist portion in a direction approximately orthogonal to the longitudinal axis of the device and wherein the holding member further comprises an open groove extending along the strut portion in a direction approximately parallel with the longitudinal axis of the device.

5. An implantable cardiac stimulation device including a pulse generator and a power source, a shell that contains the pulse generator and power source and extends along a longitudinal axis of the device from a proximal end wall to a distal end wall thereof, a fixation member located in proximity to the distal end wall, and a holding member; the holding member comprising:

a loop element including a first segment and a second segment, the first and second segments each having a terminal end, each terminal end being coupled to the device, on opposite sides thereof, in proximity to the end wall, and the first and second segments extending proximally from the terminal ends thereof; and an engagement element coupled to the loop element, between the first and second segments thereof, and being spaced proximally from the proximal end wall, the engagement element having a maximum dimension of a radial profile thereof that is less than a maximum diameter of the shell;

wherein, the first and second segments of the loop element are initially formed to give the loop element an opening located between the engagement element and the proximal end wall;

the first and second segments have a flexibility to be compressed together between the engagement element and the proximal end wall, in a direction that is approximately orthogonal to the longitudinal axis of the device; and a maximum dimension of a radial profile of the first and second segments, together, when the segments are compressed together, is less than the maximum dimension of the radial profile of the engagement element.

6. The device of claim 5, wherein the first and second segments of the loop element of the holding member, in proximity to the terminal ends thereof, bend away from one another in the proximal direction in order to define corresponding recesses between the loop element and the proximal end wall.

7. The device of claim 5, wherein the engagement element of the holding member has a generally spherical form.

8. The device of claim 5, wherein the first and second segments of the loop element of the holding member are resilient.

* * * * *